United States Patent
Miyauchi et al.

(10) Patent No.: US 7,970,623 B2
(45) Date of Patent: Jun. 28, 2011

(54) METHOD OF DETERMINING MAINTENANCE SERVICE IN ACCORDANCE WITH MEDICAL EQUIPMENT CONDITION

(75) Inventors: Akihiro Miyauchi, Tochigi-ken (JP); Yoichi Takada, Tochigi-ken (JP); Takuzo Takayama, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1492 days.

(21) Appl. No.: 10/946,095

(22) Filed: Sep. 22, 2004

(65) Prior Publication Data
US 2005/0103354 A1 May 19, 2005

(30) Foreign Application Priority Data

Sep. 24, 2003 (JP) .................. 2003-331397
Sep. 10, 2004 (JP) .................. 2004-264049

(51) Int. Cl.
*G06Q 10/00* (2006.01)
*G08B 17/12* (2006.01)
(52) U.S. Cl. .......................... 705/2; 340/600
(58) Field of Classification Search .......... 705/2–3; 378/4; 707/201; 700/79; 702/184; 701/29; 709/227
See application file for complete search history.

(56) References Cited

U.S. PATENT DOCUMENTS

| 4,853,946 | A | * | 8/1989 | Elliott et al. ............... 378/4 |
| 5,786,994 | A | * | 7/1998 | Friz et al. ................... 700/79 |
| 6,336,065 | B1 | * | 1/2002 | Gibson et al. .............. 701/29 |
| 6,810,406 | B2 | * | 10/2004 | Schlabach et al. ........ 707/201 |
| 6,912,481 | B2 | * | 6/2005 | Breunissen et al. ...... 702/184 |
| 2002/0049562 | A1 | | 4/2002 | Hahn |
| 2002/0198997 | A1 | * | 12/2002 | Linthicum et al. ........ 709/227 |

FOREIGN PATENT DOCUMENTS

| EP | 1 160 716 A2 | 12/2001 |
| EP | 1 174 817 A2 | 1/2002 |
| JP | 2002-83076 | 3/2002 |
| JP | 2002-236758 | 8/2002 |
| JP | 2003-316941 | 11/2003 |

* cited by examiner

*Primary Examiner* — Luke Gilligan
*Assistant Examiner* — Joseph Burgess
(74) *Attorney, Agent, or Firm* — Oblon, Spivak, McClelland, Maier & Neustadt, L.L.P.

(57) ABSTRACT

A method of managing at least one maintenance work on a medical equipment installed in a medical facility, starts by collecting condition information of the medical equipment. The method continues by determining the maintenance work on the medical equipment based on the collected condition information, and making it possible to provide a maintenance staff with information of the determined maintenance work.

44 Claims, 12 Drawing Sheets

| EQUIPMENT ID:002523 | EQUIPMENT ID:002525 | EQUIPMENT ID:002526 | EQUIPMENT ID:511203 |
|---|---|---|---|---|---|
| REPLACE/INSTALL DATE | PART NUMBERS | REPLACEMENT REASONS | MANUFACTURE SERIAL NUMBERS | .. | .. |
| 1/10/2002 | ABC-001234/A | INSTALLATION | 2556326 | .. | .. |
| 1/10/2002 | ABC-001255/C | INSTALLATION | 2556256 | .. | .. |
| 1/10/2002 | ABC-001267/B | INSTALLATION | 2556381 | .. | .. |
| 1/10/2002 | ABC-001335/A | INSTALLATION | 2556334 | .. | .. |
| 1/10/2002 | ABC-001423/A | INSTALLATION | 2552593 | .. | .. |
| .. | .. | .. | .. | .. | .. |
| 1/19/2003 | ABC-001255/D | PERIODIC REPLACEMENT | 2557322 | .. | .. |
| 1/19/2003 | ABC-001267/B | PERIODIC REPLACEMENT | 2558655 | .. | .. |
| 1/19/2003 | ABC-001335/B | PERIODIC REPLACEMENT | 2559556 | .. | .. |
| 1/27/2003 | ABC-001423/B | FAILURE REPLACEMENT | 2556528 | .. | .. |
| .. | .. | .. | .. | .. | .. |

FIG. 2

| | EQUIPMENT ID:002523 | EQUIPMENT ID:002525 | EQUIPMENT ID:002526 | EQUIPMENT ID:511203 |
|---|---|---|---|---|
| DATE | ACCUMULATED POWERED TIME (h) | ACCUMULATED RADIATION TIME (sec) | ACCUMULATED ROTATION NUMBERS | .. |
| 1/18/2003 | 2340.7 | 241235.6 | 512369.2 | .. |
| 1/19/2003 | 2348.5 | 241869.3 | 520121.9 | .. |
| 1/20/2003 | 2349.8 | 242001.0 | 520366.1 | .. |
| 1/21/2003 | 2355.0 | 242621.8 | 520786.8 | .. |
| 1/22/2003 | 2364.2 | 243599.0 | 522603.3 | .. |
| 1/23/2003 | 2370.8 | 244258.6 | 523251.4 | .. |
| 1/24/2003 | 2378.1 | 245155.7 | 525098.9 | .. |
| 1/25/2003 | 2388.0 | 246160.4 | 527360.2 | .. |
| 1/26/2003 | 2390.1 | 246311.2 | 527687.6 | .. |
| 1/27/2003 | 2390.1 | 246311.2 | 527687.6 | .. |
| .. | .. | .. | .. | .. |

FIG. 3

| | EQUIPMENT ID:002523 | EQUIPMENT ID:002525 | EQUIPMENT ID:002526 | | EQUIPMENT ID:511203 | |
|---|---|---|---|---|---|---|
| | | TEMPERATURE (°C) | | | HUMIDITY (%) | |
| DATE | MAX. | MAX. TIME | MIN. | MIN. TIME | AVE. | FILE NAME | MAX. | MAX. TIME | MIN. | .. |
| 1/18/2003 | 15.5 | 14:23 | 8.0 | 5:30 | 11.2 | 030118.csv | 33.5 | 14:23 | 12.3 | .. |
| 1/19/2003 | 15.4 | 13:35 | 6.8 | 4:56 | 9.8 | 030119.csv | 35.5 | 13:35 | 10.2 | .. |
| 1/20/2003 | 15.2 | 15:00 | 4.5 | 6:02 | 10.2 | 030120.csv | 34.6 | 15:00 | 13.0 | .. |
| 1/21/2003 | 13.2 | 14:20 | 2.3 | 6:13 | 7.6 | 030121.csv | 37.8 | 14:20 | 9.0 | .. |
| 1/22/2003 | 13.2 | 14:02 | 3.8 | 6:24 | 8.5 | 030122.csv | 36.3 | 14:02 | 7.5 | .. |
| 1/23/2003 | 12.2 | 14:13 | 5.9 | 5:34 | 9.6 | 030123.csv | 34.2 | 14:13 | 11.6 | .. |
| 1/24/2003 | 10.2 | 11:33 | 5.6 | 4:43 | 8.1 | 030124.csv | 35.8 | 11:33 | 12.8 | .. |
| 1/25/2003 | 14.5 | 12:39 | 2.3 | 3:56 | 9.9 | 030125.csv | 33.3 | 12:39 | 13.2 | .. |
| 1/26/2003 | 14.3 | 13:00 | 8.5 | 6:34 | 11.0 | 030126.csv | 36.5 | 13:00 | 16.5 | .. |
| 1/27/2003 | 13.0 | 12:25 | 6.8 | 7:23 | 9.7 | 030127.csv | 37.0 | 12:25 | 18.6 | .. |
| .. | .. | .. | .. | .. | .. | .. | .. | .. | .. | .. |

FIG. 4

| DATE | EQUIPMENT ID:002523 IMAGE QUALITY PARAMETER A | | | | EQUIPMENT ID:002525 | | | | EQUIPMENT ID:002526 IMAGE QUALITY PARAMETER B | | | EQUIPMENT ID:511203 IMAGE QUALITY PARAMETER C | | |
|---|---|---|---|---|---|---|---|---|---|---|---|---|---|---|
| | TYPE1 | TYPE2 | TYPE3 | TYPE4 | TYPE1 | TYPE2 | TYPE3 | TYPE4 | TYPE1 | TYPE2 | TYPE3 | TYPE1 | TYPE2 | .. |
| 1/18/2003 | 978.1 | -1017.6 | -97.9 | 122.5 | 5.05 | 1.9 | 0.13 | | 0.03 | 20.00 | | | | .. |
| 1/19/2003 | 976.8 | -1019.0 | -97.4 | 122.3 | 4.99 | 1.83 | 0.14 | | 0.03 | 18.00 | | | | .. |
| 1/20/2003 | 978.5 | -1018.4 | -100.4 | 123.2 | 4.98 | 1.85 | 0.13 | | 0.03 | 16.00 | | | | .. |
| 1/21/2003 | 984.2 | -1013.0 | -103.7 | 120.6 | 4.98 | 2.09 | 0.23 | | 0.05 | 18.00 | | | | .. |
| 1/22/2003 | 988.8 | -1013.0 | -104.1 | 118.3 | 4.99 | 2.34 | 0.26 | | 0.05 | 20.00 | | | | .. |
| 1/23/2003 | 990.7 | -1011.2 | -104.7 | 121.2 | 4.97 | 2.15 | 0.30 | | 0.06 | 19.00 | | | | .. |
| 1/24/2003 | 981.6 | -1010.2 | -101.6 | 121.6 | 5.04 | 1.93 | 0.20 | | 0.04 | 18.00 | | | | .. |
| 1/25/2003 | 988.4 | -1014.9 | -104.1 | 119.7 | 4.97 | 1.9 | 0.22 | | 0.04 | 18.00 | | | | .. |
| 1/26/2003 | 985.0 | -1013.0 | -102.9 | 119.8 | 4.97 | 2 | 0.17 | | 0.03 | 22.00 | | | | .. |
| 1/27/2003 | 988.7 | -1015.5 | -103.6 | 120.1 | 4.90 | 2.05 | 0.17 | | 0.03 | 21.00 | | | | .. |
| .. | .. | .. | .. | .. | .. | .. | .. | | .. | .. | | | | .. |

| PART NUMBERS 3311 | BENCHMARK INFORMATION 3312 | WORK IDs 3313 |
|---|---|---|
| ABC·001255/A | (3222) > 3600 | 10 01 00 |
| ABC·001255/B | (3222) > 5800 | 10 01 00 |
| ABC·001255/C | (3222) > 6900 | 10 01 00 |
| ABC·001255/D | (3222) > 10000 | 10 01 00 |
| ABC·001267/A | (3223) > 100000 | 10 03 02 |
| ABC·001267/B | (3223) > 200000 | 10 03 02 |
| ABC·001423/A | (3224) > 200000 | 11 06 00 |
| ABC·001423/B | (3224) > 250000 | 11 06 00 |
| ABC·001423/C | (3224) > 300000 | 11 06 00 |
| — | MAX.:(3233) > 60 | 10 02 01 |
| — | IMAGE QUALITY PARAMETER B:TYPE1 > 5.5 | 11 05 00 |
| .. | .. | .. |

| 332 | 3321 | 3322 | 3323 | 3324 | 3325 | 3326 |
|---|---|---|---|---|---|---|
| | WORK IDs | WORK PROCEDURE REFERENCES | PART REPLACEMENT | PART NUMBERS | STANDARD WORK TIME | CONCURRENT WORK IDs |
| | 10 01 00 | DOCUMENT # 98990 SEC 10-3 | YES | ABC-001255 | 1H | 10 02 01<br>11 05 00 |
| | 10 03 02 | DOCUMENT # 12334 SEC 3-3 | YES | ABC-001267 | 0.5H | 10 02 01<br>11 05 00 |
| | 11 06 00 | DOCUMENT # 89891 SEC 10-3 | YES | ABC-001423 | 2H | 10 02 01<br>11 05 00 |
| | 10 02 01 | DOCUMENT # 45666 SEC 5-8 | NO | | 1H | 10 01 00 |
| | 11 05 00 | DOCUMENT # 00896 SEC 2-4 | NO | | 3H | 10 01 00 |
| | .. | .. | .. | .. | .. | .. |

| | 3411 | 3412 | 3413 | 3414 |
|---|---|---|---|---|
| 341 | FAILURE DATE | FAILURE PART NUMBERS | QUALITY DETERIORATED SUBJECTS | EQUIPMENT IDs |
| | 1/10/2002 | ABC·001234/A | | 2556326 |
| | 3/25/2002 | ABC·001255/C | | 2556256 |
| | 4/19/2002 | ABC·001267/B | | 2556381 |
| | 5/3/2002 | ABC·001335/A | | 2556334 |
| | 7/21/2002 | ABC·001423/A | | 2552593 |
| | 1/19/2003 | | IMAGE QUALITY PARAMETER A TYPE1 | 2557322 |
| | 1/19/2003 | | IMAGE QUALITY PARAMETER B TYPE2 | 2558655 |
| | 1/19/2003 | ABC·001335/B | | 2559556 |
| | 1/27/2003 | ABC·001423/B | | 2556528 |
| | .. | .. | .. | .. |

METHOD OF DETERMINING MAINTENANCE SERVICE IN ACCORDANCE WITH MEDICAL EQUIPMENT CONDITION

CROSS-REFERENCE TO RELATED APPLICATION

This application is based upon and claims the benefit of priority from prior Japanese Patent Applications Nos. P2003-331397, filed on Sep. 24, 2003 and P2004-264049, filed on Sep. 10, 2004, the entire contents of which are incorporated herein by reference.

BACKGROUND OF THE INVENTION

1. Field of the Invention

The present invention relates to a method of managing a maintenance work on a medical equipment. The present invention also relates to a maintenance system which manages a maintenance work on a medical equipment.

2. Discussion of the Background

When a medical equipment such as a medical imaging apparatus or a laboratory equipment is installed in a medical facility such as a hospital, a maintenance service contract may be agreed between the hospital and a medical equipment supplier such as, for example, a medical equipment manufacturer, a medical equipment sales company, or a maintenance service provider. The maintenance service contract is typically agreed for the purpose of maintaining a quality and a performance of the medical equipment at more than a certain level, in consideration with a request from the medical facility and presuming a future operation condition of the medical equipment. In a typical maintenance service contract, it is agreed to conduct predetermined maintenance works at predetermined intervals as periodic services. In practice, the periodic services may be conducted based on a maintenance service instruction manual prepared in advance. That is, maintenance works instructed in the maintenance service instruction manual may be conducted by a maintenance staff.

It may be a recent trend that a guarantee according to the maintenance service contract can be differentiated in accordance with a contract fee. What is guaranteed includes, for example, a maintained level of the quality or of the performance of the medical equipment. For example, an image quality is guaranteed at more than a specific quantitative level. Also, for example, it may be guaranteed to keep an actual operating time (or an uptime) of the medical equipment in a time period when the medical equipment should be operated in the medical facility to be more than a predetermined time period.

In some cases, it is difficult for a regular maintenance staff to conduct the maintenance works to meet the agreed guarantee level. In this case, an expert engineer may be asked to travel to the medical facility. In another cases, when a part, an accessory, a component, a unit, and/or the like (hereinafter referred to as a part) used in the medical equipment has become degraded or deteriorated so that the agreed guarantee level cannot be met, it may be necessary to replace the part with a new one. If such a new part is not in stock in a local service office where the maintenance staff is usually located, it may be necessary to send the part by air so as to supply the maintenance staff with the part as soon as possible. Therefore, it has largely cost to reduce time to meet the agreed guarantee level in a prior art.

One of solutions for the above problem is a remote maintenance system using a public communication network such as a telephone line network or the Internet. According to the improvement of information communication networks, the remote maintenance system is more often used to analyze the status of the medical equipment. For example, Japanese Patent Application Publication No. PH06-62130 describes that a log, a set-up file, image data, and the like stored in a medical equipment installed in a medical facility are read out from a remote maintenance computer through a network in response to an error (or a failure) notice from the medical facility. Based on the read-out information, the error may be recreated and the reason of the error may be determined. Accordingly, since it has become possible to cope with the error in advance of a periodic service by using the remote maintenance system, it may become possible to reduce time in an actual periodic service. In addition, a cost may also be reduced for the periodic service.

However, the maintenance works to be conducted in the periodic service have been limited to those determined in a maintenance service instruction manual prepared in advance, as described above. In other words, the maintenance works have not been conducted in light of actual conditions of the medical equipment such as, for example, the frequency of using the medical equipment, an environmental condition change in the use of the medical equipment, and/or a part replacement for improving a characteristic of a part used in the medical equipment.

Each medical equipment is usually used in a different condition from others, particularly when it is installed in a different place or in a different medical facility. Therefore, as long as the maintenance works are conducted in accordance with a conventional maintenance service instruction manual, it is difficult to take an action for the deterioration of functions and/or qualities caused due to the individual condition of the medical equipment. Even if the remote maintenance system is introduced, such an action may be passed over or not considered sufficiently. Accordingly, even if the conventional periodic service is conducted, the medical equipment may be subject to an unexpected problem such as, for example, an error occurrence and a breakdown. This results again in requiring a large cost in order to fix the problem.

Further, if it is a full-time maintenance staff for the medical facility or a highly-experienced maintenance staff, such a maintenance staff may manage to conduct maintenance works in accordance with conditions of the medical facility, using his or her skills based on experience and information obtained individually. However, if it is not a full-time maintenance staff for the medical facility, a less experienced maintenance staff, or a maintenance staff for a wide variety of medical equipments, it may be necessary for the full-time maintenance staff for the medical facility or the like to clearly instruct specific maintenance works or a benchmark of conducting a specific maintenance work to the less experienced maintenance staff or the like.

SUMMARY OF THE INVENTION

According to the first aspect of the present invention, there is provided a method of managing at least one maintenance work on a medical equipment installed in a medical facility. The method begins by collecting condition information of the medical equipment. The method continues by determining the maintenance work on the medical equipment based on the collected condition information. The method further continues by making it possible to provide a maintenance staff with information of the determined maintenance work.

According to the second aspect of the present invention, there is provided a method of managing a maintenance work on a medical equipment installed in a medical facility. The method begins by designating equipment identification information identifying the medical equipment. The method continues by collecting condition information of the medical equipment identified by the designated equipment identification information, and comparing the collected condition information to reference information. The method further continues by determining work identification information identifying the maintenance work based on the comparison, and making it possible to provide a maintenance staff with information of the maintenance work identified by the determined work identification information.

According to the third aspect of the present invention, there is provided a maintenance system for managing at least one maintenance work on a medical equipment installed in a medical facility. The system includes a collecting unit, a controller, and a provider. The collecting unit is configured to collect condition information of the medical equipment. The controller is coupled to the collecting unit and is configured to determine the maintenance work on the medical equipment based on the collected condition information. The provider is coupled to the controller and is configured to make it possible to provide a maintenance staff with information of the determined maintenance work.

According to the fourth aspect of the present invention, there is provided a maintenance system for managing a maintenance work on a medical equipment installed in a medical facility. The system includes a designator, a memory, a controller, and a provider. The designator is configured to designate equipment identification information identifying the medical equipment. The memory is coupled to the designator and is configured to store the equipment identification information, condition information of the medical equipment identified by the equipment identification information, benchmark information for comparing the condition information to reference information, and work identification information identifying the maintenance work resulting from a comparison based on the benchmark information in a related manner. The controller is coupled to the memory and is configured to determine the work identification information based on the designated equipment identification information. The provider is coupled to the controller and is configured to make it possible to provide a maintenance staff with information of the maintenance work identified by the determined work identification information.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 2 is an illustration showing an example of a replacement part managing table of a medical equipment condition database according to the embodiment;

FIG. 3 is an illustration showing an example of an operating condition managing table of the medical equipment condition database according to the embodiment;

FIG. 4 is an illustration showing an example of an environmental condition managing table of the medical equipment condition database according to the embodiment;

FIG. 5 is an illustration showing an example of a quality managing table of the medical equipment condition database according to the embodiment;

FIG. 6 is an illustration showing an example of a benchmark table of a work procedure database according to the embodiment;

FIG. 7 is an illustration showing an example of a work procedure table of the work procedure database according to the embodiment;

FIG. 8 is an illustration showing an example of a failure record table of a failure record database according to the embodiment;

DESCRIPTION OF THE PREFERRED EMBODIMENTS

Embodiments of a maintenance system will be described with reference to the accompanying drawings.

Figure 1:
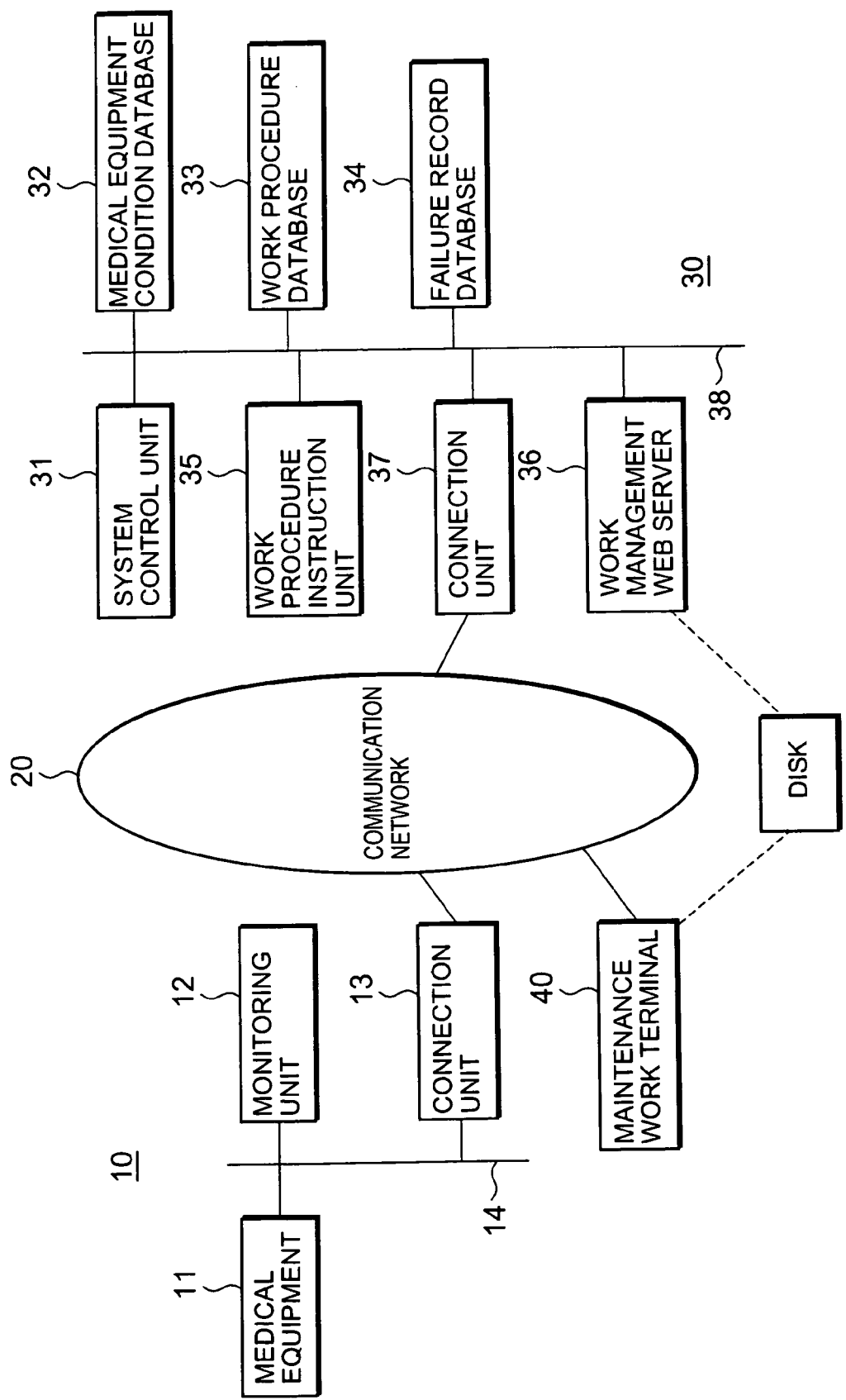
FIG. 1 is a block diagram showing an exemplary configuration of a system for explaining a maintenance system according to an embodiment.

FIG. 1 is a block diagram showing an exemplary configuration of a system for explaining a maintenance system according to an embodiment. As shown in FIG. 1, a hospital 10 is connected to a service center 30 through a communication network. The hospital 10 is an example of a medical facility. Any place where a medical practice is conducted may be included in the medical facility whether it is small or large. For example, the medical facility may be a clinic, a medical practitioner, and an emergency medical center, besides the hospital. The communication network 20 is an example of communication lines. The hospital 10 may be connected to the service center 30 through any type or purpose of lines such as, for example, optical communication lines, radio communication lines, wired lines, the Internet, telephone lines, public lines, or private lines. The service center 30 may be provided, for example, in a medical equipment manufacturer, a sales company, a maintenance service provider, a subsidiary or an affiliate of one or more of these companies, or a company under the control of one or more of these companies.

The service center 30 may also be connected to a maintenance work terminal 40 through the communication network 20. The maintenance work terminal 40 may be used, for example, in the hospital 10 by a maintenance staff who conducts periodic services on a medical equipment 11. The maintenance work terminal 40 may be, for example, a portable personal computer (PC) and may include a transmission feature of requesting information of maintenance works to the service center 30 through the communication network 20, a feature of receiving information of the maintenance works from the service center 30, a feature of storing information, and a feature of displaying information.

The maintenance work terminal 40 may alternatively be connected to the service center 30 through a communication line which is a different type of a communication line connecting between the hospital 10 and the service center 30. Further alternatively, all or part of the information to be provided from the service center 30 to the maintenance work terminal 40 may be stored by a driver (as a provider) in a portable memory medium such as, for example, a DVD, a CD, or a floppy disk (FD). After the storage, the portable memory medium may be sent to the maintenance staff by mail or directly handed over through a person. In response that the maintenance staff sets the portable memory medium in the maintenance work terminal 40, the stored information is read out and displayed in the maintenance work terminal 40. Accordingly, all or part of the information to be provided from the service center 30 to the maintenance work terminal 40 can be supplied to the maintenance staff.

Furthermore, the third terminal may obtain the information of the maintenance works through the communication network 20 or the portable memory medium. The received information may be supplied to the maintenance work terminal 40 by downloading, copying, or any other possible means.

The hospital 10 may include the medical equipment 11, a monitoring unit 12, a connection unit 13, and a bus 14 connecting these equipment and units. The bus 14 may be a part of a local area network (LAN) provided in the hospital 10. The medical equipment 11 is typically used for the purpose of a medical examination, a medical treatment, or the like in the medical facility and may be, for example, a medical imaging apparatus or a laboratory equipment. The medical imaging apparatus may be, for example, an X-ray diagnosis apparatus, an X-ray computed tomography (CT) apparatus, a magnetic resonance imaging (MRI) apparatus, a nuclear medicine diagnosis apparatus, an ultrasound diagnosis apparatus, an endoscope apparatus, or the like.

The monitoring unit 12 monitors conditions of the medical equipment 11. For example, the monitoring unit 12 may monitor use frequency of the medical equipment, which may be represented by its operating time and/or the like. The monitoring unit 12 may also monitor an environmental condition in the use of the medical equipment 11, which may be represented by the temperature and/or the humidity at a predetermined part of the medical equipment 11 or at a nearby place of the medical equipment 11. The monitoring unit 12 may further monitor a quality of the medical equipment 11, which may be represented by a power voltage or an image quality. The monitored conditions are collected as CONDITION information of the medical equipment 11 or fundamental information of the CONDITION information (hereinafter simply referred to as CONDITION information). The connection unit 13 may transmit the CONDITION information to the service center 30 through the communication network 20. The connection unit 13 may be chosen to be suitable for the communication with the communication network 20.

The service center 30 may include a system control unit 31, a medical equipment condition database 32, a work procedure database 33, a failure record database 34, a work procedure instruction unit 35, a work management WEB server 36, a connection unit 37, and a bus 38 connecting these units, databases, and server.

The system control unit 31 controls and manages all or part of the units, the databases, and the server included in the service center 30. The system control unit 31 may also control a maintenance management (to be described later). The medical equipment condition database 32 receives the CONDITION information collected in the monitoring unit 12 through the condition unit 13, the communication network 20, and the connection unit 37. The received CONDITION information may be stored and managed in table forms in every equipment ID (equipment identification information), for example, as shown in an operating condition managing table 322 of FIG. 3, an environmental condition managing table 323 of FIG. 4, and a quality managing table 324 of FIG. 5.

The work procedure database 33 is a database storing information of the maintenance works. The work procedure database 33 may store and manage, for example, benchmarks of conducting specific maintenance works and information which is useful, helpful, and/or valuable for the maintenance staff (work procedures) in table forms, as shown in a benchmark table 331 of FIG. 6 and a work procedure table 332 of FIG. 7. The failure record database 34 may store and manage, for example, all or part of the information of conducting periodic services in the past in table forms, as shown in a failure record table 341 of FIG. 8.

The work procedure instruction unit 35 may store and manage, for example, a maintenance work list extracted from the work management WEB server 36 and work procedures extracted from the work procedure table 332 in order to provide the maintenance staff with the list and the procedures. The work management WEB server 36 may store and manage as a provider, for example, the maintenance work list determined based on, information stored in the tables of the medical equipment condition database 32 and information stored in the tables of the work procedure database 33. The maintenance work list may include maintenance works which the maintenance staff should conduct. The maintenance work list may be prepared in every equipment ID.

The connection unit 37 may transmit as a provider to the maintenance work terminal 40 through the communication network 20, for example, information of the work procedures stored in the work procedure instruction unit 35 as a part of information of maintenance works. The connection unit 37 may be chosen to be suitable for the communication with the communication network 20.

Each table mentioned above will be described below.

FIG. 2 is an illustration showing an example of a replacement part managing table 321 of the medical equipment condition database 32. As shown in FIG. 2, the replacement part managing table 321 includes replacement/installation date 3211, part numbers 3212, replacement reasons 3213, manufacture serial numbers 3214, and the like in a related manner. The above date, numbers, reasons, and the like may be related to one another in every equipment ID. According to the replacement part managing table 321, the system control unit 31 which has accessed to the replacement part managing table 321 may obtain information of when and in what reason a part identified by a specific part number was provided in the medical equipment 11 identified by a specific equipment ID. In this embodiment, each of the part numbers 3212 includes a number and a revision mark (e.g., /A). The revision mark may indicate a revision version and be updated to A, B, C, . . . as a part with the same number is updated. Therefore, the system control unit 31 may be able to realize which revision version of a specific number in the part numbers 3212 had a problem. Hereinafter, a 'part number' means to include a number and a revision mark unless specifically described.

FIG. 3 is an illustration showing an example of the operating condition managing table 322 of the medical equipment condition database 32. As shown in FIG. 3, the operating condition managing table 322 includes date 3221, an accumulated powered time 3222 showing accumulated hours of time when the medical equipment 11 is supplied power, an accumulated X-ray radiation time 3223 expressed in seconds, accumulated rotation numbers 3224 showing accumulated numbers of gantry rotation in the medical equipment 11, and the like in a related manner. The above date, time, numbers, and the like may be related to one another in every equipment ID. Information stored in this operating condition managing table 322 may be the CONDITION information. According to the operating condition managing table 322, the system control unit 31 which has accessed to the operating condition managing table 322 may obtain information of what an accumulated powered time until a specific date is in hours. The system control unit 31 may also obtain information of what an accumulated X-ray radiation time in the accumulated powered time is in seconds. Further, the system control unit 31 may obtain information of how many times a gantry of the medical equipment 11 has been rotated in the accumulated powered time.

FIG. 4 is an illustration showing an example of the environmental condition managing table 323 of the medical equipment condition database 32. As shown in FIG. 4, the environmental condition managing table 323 includes date 3231, temperature 3232, humidity 3233, and the like in a related manner. The above date, temperature, humidity, and the like may be related to one another in every equipment ID. The temperature 3232 and the humidity 3233 may include further detailed information.

For example, the temperature 3232 may include maximum and minimum temperatures of each date 3231 which were recorded where the medical equipment 11 is installed and the recorded time. The temperature 3232 may also include an average temperature of each date 3231. The temperature 3232 may further include a name of a file recording all the temperature and time information recorded in each date 3231 which is a basis of the maximum, minimum, and average temperatures and their recorded time. The file may be linked to in order to refer to the recorded temperature and time information.

The humidity 3233 may include maximum and minimum humidities of each date 3231 which were recorded where the medical equipment 11 is installed and the recorded time. The humidity 3233 may also include an average humidity of each date 3231 (not shown in FIG. 4). The humidity 3233 may further include a name of a file recording all the humidity and time information recorded in each date 3231 which is a basis of the maximum, minimum, and average humidities and their recorded time (not shown in FIG. 4). The file may be linked to in order to refer to the recorded humidity and time information.

The temperature information and humidity information may be recorded in the same file. The file(s) may be data file(s) recording environmental condition information such as the temperature and the humidity sampled (or measured) at predetermined intervals in every day. The recorded environmental information may be distinguished by calendar day.

The above-mentioned recording place where the medical equipment 11 is installed may be, for example, a predetermined part of the medical equipment 11 or a nearby place of the medical equipment 11. Sampling the temperature and the humidity at the nearby place may include sampling the room temperature and the room humidity in a room or place where the medical equipment 11 is installed. Sampled and recorded environmental condition information is not limited to the temperature and the humidity. The maximum, minimum, and average temperatures and humidities may be based on the temperatures and humidities sampled in twenty-four (24) hours of each date 3231, in a predetermined time period of each date 3231, or in a time period while the medical equipment 11 is supplied power.

Information stored in this environmental condition managing table 323 may be the CONDITION information. According to the environmental condition managing table 323, the system control unit 31 which has accessed to the environmental condition managing table 323 may obtain information of the environmental condition information regarding a specific date or a specific period.

FIG. 5 is an illustration showing an example of the quality managing table 324 of the medical equipment condition database 32. As shown in FIG. 5, the quality managing table 324 includes date 3241, image quality parameters A 3242, image quality parameters B 3243, and the like in a related manner. The above date, parameters, and the like may be related to one another in every equipment ID. The image quality parameter may mean, for example, resolution MTF (Modulation Transfer Function), low-contrast resolution, CT value, slice width, and/or the like. Parameters recorded in the quality managing table 324 are not limited to the image quality parameters, but may be any type of parameters which can indicate quality evaluation of the medical equipment 11. Information stored in this quality managing table 324 may be the CONDITION information.

In FIG. 5, the image quality parameters A 3242 and B 3243 may be divided into further different types of parameter information. According to the quality managing table 324, the system control unit 31 which has accessed to the quality managing table 324 may obtain information of various types of parameter values on specific date and/or relationship among these parameter values.

FIG. 6 is an illustration showing an example of the benchmark table 331 of the work procedure database 33. As shown in FIG. 6, the benchmark table 331 includes part numbers 3311, benchmark information 3312, work IDs 3313, and the like in a related manner. The benchmark information 3312 is a standard for determining whether the maintenance work should be conducted or not. The CONDITION information is applied to the left side of the benchmark information 3312 and is compared to reference information in the right side of the benchmark information 3312 by the system control unit 31. When the relationship between the left and the right sides of the benchmark information is satisfied, corresponding work ID 3313 in the benchmark table 331 is determined by the system control unit 31 so that the maintenance work identified by the work ID 3313 can be conducted by the maintenance staff.

For example, in the first row of the benchmark table 331 shown in FIG. 6, the left side of the benchmark information 3312 showing '(3222)' indicates that the accumulated powered time 3222 shown in the operating condition managing table 322 is applied to the left side. For example, the accumulated powered time '2390.1 hours' on Jan. 27, 2003 is compared to the reference information '3600 hours'. Since the accumulated powered time '2390.1 hours' is smaller than the reference information '3600 hours', the benchmark information 3312 in the first row of the benchmark table 331 is not satisfied. If, however, the benchmark information 3312 in the first row was satisfied, the work ID '10 01 00' recorded also in the first row of the benchmark table 331 would be determined so that the maintenance work identified by the work ID '10 01 00' can be conducted by the maintenance staff. The maintenance work identified by the work ID '10 01 00' may be conducted in relation to a part identified by the part number ABC-001255/A also recorded in the first row of the benchmark table 331. In other word, the comparison result of the benchmark information 3312 may be originated from failure of the part identified by the part number ABC-001255/A.

Further in FIG. 6, there is recorded benchmark information 3312 which does not have corresponding part numbers 3311 in rows 3314. This is a case that the benchmark information 3312 may not relate to specific parts identified by the part numbers 3311. (Overall) features such as, for example, the image quality parameter, the temperature, and the humidity may be applied to the left side of the benchmark information 3312 and is compared to the reference information in the right side of the benchmark information 3312 by the system control unit 31. When the relationship between the left and the right sides of the benchmark information 3312 is satisfied, corresponding work ID 3313 in the benchmark table 331 is determined by the system control unit 31 so that the maintenance work identified by the work ID 3313 can be conducted by the maintenance staff.

For example, in the third row from the bottom of the benchmark table 331 shown in FIG. 6, the left side of the benchmark information 3312 showing 'MAX.: (3233)' indicates that the maximum humidity of the humidity 3233 shown in the environmental condition managing table 323 is applied to the left side. For example, the maximum humidity '37.0%' on Jan. 27, 2003 is compared to the reference information '60%'. Since the maximum humidity '37.0%' is smaller than the reference information '60%', the benchmark information 3312 in the third row from the bottom of the benchmark table 331 is not satisfied. If, however, the benchmark information 3312 in the third row from the bottom was satisfied, the work ID '10 02 01' recorded also in the third row from the bottom of the benchmark table 331 would be determined so that the maintenance work identified by the work ID '10 02 01' can be conducted by the maintenance staff. The maintenance work identified by the work ID '10 02 01' may not be conducted in relation to any specific parts. In other word, the comparison result of the benchmark 3312 may not be originated from failure of any specific parts.

FIG. 7 is an illustration showing an example of the work procedure table 332 of the work procedure database 33. As shown in FIG. 7, the work procedure table 332 includes work IDs 3321, work procedure references 3322, part replacement 3323, part numbers 3324, standard work time 3325, concurrent work IDs 3326, and the like in a related manner.

The work procedure references 3322 are identified by the work IDs 3321 and show references to be referred by the maintenance staff in order to conduct the maintenance work. Each of the work procedure references 3322 instructs a document number, a section number, and a page number. For example, in the first row of the work procedure table 332 shown in FIG. 7, the work procedure reference 3322 identified by the work ID '10 01 00' instructs to refer to page 3 in the section 10 of the document No. 98990.

The part replacement 3323 indicates whether part replacement is required or not when the maintenance work identified by the work ID 3321 is conducted by the maintenance staff. When the part replacement is required, that is, the part replacement 3323 shows 'yes', a part identified by the part number 3324 is required to be replaced. The standard work time 3325 indicates an approximate time required for the maintenance staff to complete the maintenance work identified by the work ID 3321. According to a type of the maintenance work, two or more maintenance works may be concurrently conducted by the maintenance staff. The concurrent work ID 3326 indicates one or more work IDs identifying the maintenance works which can be concurrently conducted when the maintenance work identified by the work ID 3321 is conducted.

FIG. 8 is an illustration showing an example of the failure record table 341 of the failure record database 34. As shown in FIG. 8, the failure record table 341 includes failure date 3411, failure part numbers 3412, quality deteriorated subjects 3413, equipment IDs 3414, and the like in a related manner. The failure record table 341 shows all or part of the information of maintenance services conducted in the past by the maintenance staff.

Part numbers shown in the failure part numbers 3412 indicate information identifying parts on which the maintenance works were conducted by the maintenance staff. The system control unit 31 can recognize an equipment ID in the equipment IDs 3414 recorded in correspondence with a specific part number in the failure part numbers 3412. Also regarding a quality deteriorated parameter or the like which may not result from specific parts, the system control unit 31 can recognize an equipment ID recorded in correspondence with such a deteriorated parameter in the failure record table 341. The system control unit 31 can collect CONDITION information of the recognized equipment ID or parameters which was collected at the time indicated in the failure date 3441 from the operating condition managing table 322, the environmental condition managing table 323, the quality managing table 324, and/or the like. The system control unit 31 may then update the reference information recorded in the benchmark information 3312 of the benchmark table 331 based on the collected CONDITION information. This update will be described in detail later.

Although each table has been described in detail with reference to FIGS. 2 to 8, each table may be constructed in more detail or may be divided into two or more tables. Contrary, two or more of the above-described tables may be formed in a single table. Table format and/or construction can be changed freely in accordance with, for example, types of information to be stored, control algorithm by the system control unit 31 or others, and/or a system design of the maintenance system. One or more of the databases 32 to 34 may construct a memory.

Operations of the maintenance system configured as explained above will be described below. First, information collecting procedures will be described as a basis of the maintenance management operations.

Figure 9:
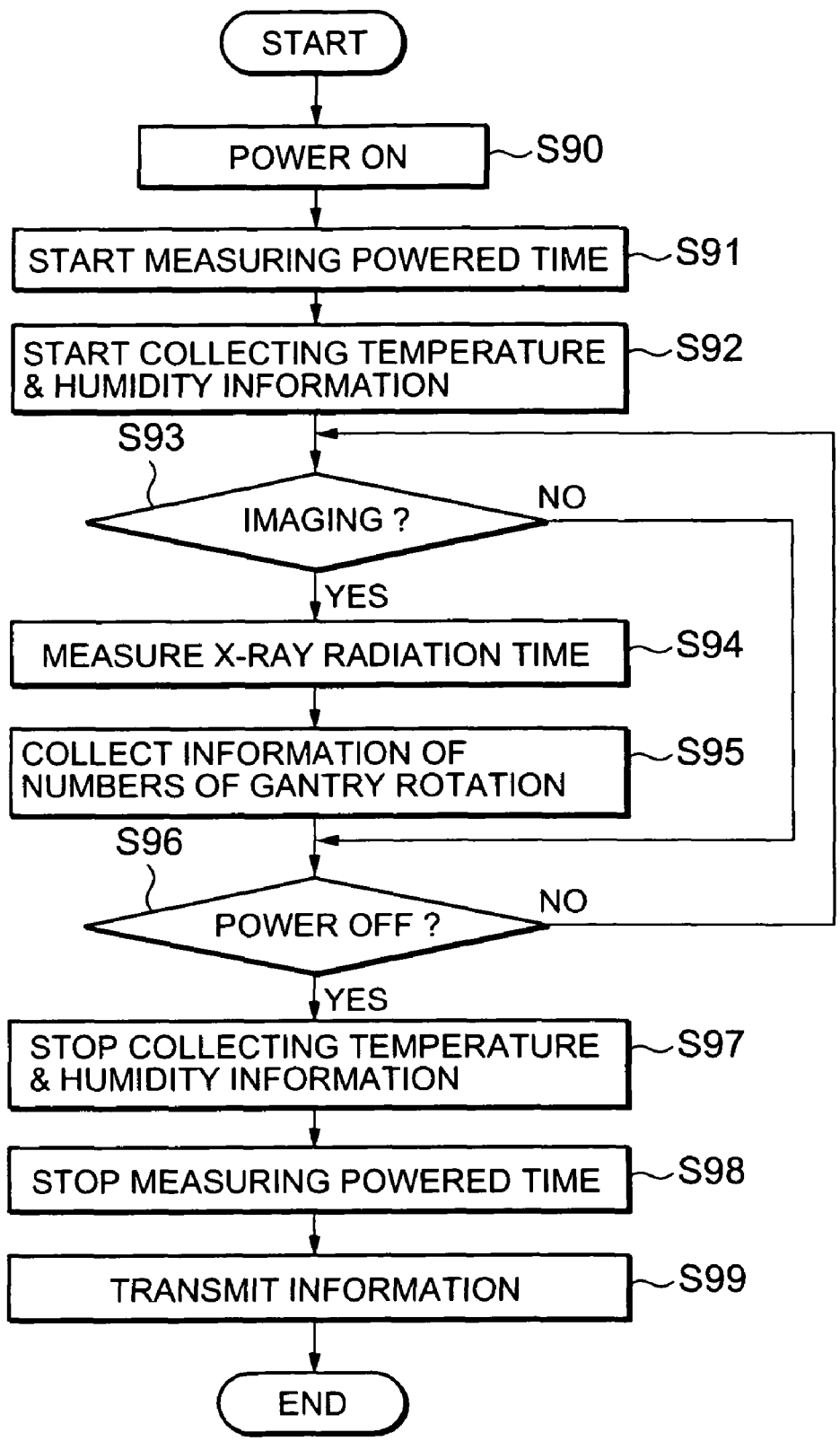
FIG. 9 is a flowchart for explaining an example of collecting various kinds of CONDITION information according to the embodiment.

FIG. 9 is a flowchart for explaining an example of collecting various kinds of CONDITION information. This flowchart shows a case of collecting powered time, X-ray radiation time, and information of the numbers of gantry rotation which can be fundamental of the accumulated powered time 3222, the accumulated X-ray radiation time 3223, and the accumulated rotation numbers 3224, respectively. This flowchart also shows a case of collecting temperature information and humidity information. Kinds of information to be collected and collecting procedures are not limited to those shown in FIG. 9.

When the medical equipment 11 is switched to power on (step S90), the monitoring unit 12 is notified of the power-on through the bus 14. In response to the notification, the monitoring unit 12 starts measuring powered time of the medical equipment 11 (step S91). Simultaneously, the monitoring unit 12 starts measuring the temperature and the humidity at a predetermined part of the medical equipment 11 or at a nearby place of the medical equipment 11. To be precise, the monitoring unit 12 starts collecting results measured by a thermometer and a hygrometer provided at a predetermined part of the medical equipment 11 or at a nearby place of the medical equipment 11 (step S92).

For example, the monitoring unit 12 may collect the measured results at predetermined intervals. The monitoring unit 12 may collect the measured results with time information of the measurement or the collection. Alternatively, the monitoring unit 12 may add time information of the collection based on a timer provided in the monitoring unit 12 to the collected measured results.

When the image equipment 11 is an X-ray CT apparatus, an operator switches to instruct rotation of a gantry provided in the medical equipment 11 so as to prepare for imaging. In response to the instruction (step S93), the gantry starts rotating. The numbers of gantry rotation may be counted in the medical equipment 11. When the operator switches to start imaging, the medical equipment 11 (i.e., X-ray tube) starts radiating X-ray so that imaging is conducted. This switching may be notified to the monitoring unit 12 through the bus 14. In response to the notification, the monitoring unit 12 starts measuring X-ray radiation time of the medical equipment 11 (step S94).

When the operator switches to terminate the imaging, the medical equipment 11 stops the X-ray radiation. The switching may be notified to the monitoring unit 12 through the bus 14. In response to the notification, the monitoring unit 12 stops measuring X-ray radiation time of the medical equipment 11. Also when the operator switches to terminate the rotation of the gantry, the gantry stops its rotation. In response to the stop of rotation, the medical equipment 11 stops counting the number of rotation. The counted number of rotation is sent to the monitoring unit 12 through the bus 14 (step S95).

Unless the medical equipment 11 is switched to power off (step S96), in every imaging (step S93) the measurement of the X-ray radiation time (step S94) and the collection of the number of rotation (step S95) are repeated.

When the medical equipment 11 is switched to power off (step S96), the monitoring unit 12 is notified of the power-off through the bus 14. In response to the notification, the monitoring unit 12 stops collecting the measured results of the temperature and the humidity (step S97). Simultaneously, the monitoring unit 12 stops measuring powered time of the medical equipment 11 (step S98).

According to the above measurement and collection in the monitoring unit 12, information of the measured or collected powered time, X-ray radiation time, number of gantry rotation, temperature, and humidity may be sent to the service center 30 through the connection unit 13 and the communication network 20 (step S99).

The transmission to the service center 30 may not be necessary to be implemented in every power-off of the medical equipment 11, but may be implemented once a day or once in a predetermined period such as, for example, once in a few days or once a week, however many times the power-on and off is repeated in one day. In this case, transmission in a time when the communication network 20 is not busy, for example, in the midnight, may help to reduce a load in the communication network 20 and accordingly other communications through the communication network 20 can not be so affected by the transmission.

Similarly, if the medical equipment 11 includes a feature of measuring and storing the measured results, the communication between the medical equipment 11 and the monitoring unit 12 may be implemented in a time when the bus 14 is not busy, for example, in the midnight. Further, if the medical equipment 11 includes a measuring and collecting feature required in the monitoring unit 12 or if the service center 30 includes such a feature, the medical equipment 11 can transmit the information directly to the service center 30 through the communication unit 13 and the communication network 20.

Furthermore, the communication between the medical equipment 11 and the monitoring unit 12, between the medical equipment 11 and the service center 30, and/or between the monitoring unit 12 and the service center 30 may be achieved without the bus 14 or the communication network 20. For example, all or part of the information to be provided may be stored in a portable memory medium such as, for example, a DVD, a CD, or a floppy disk (FD). After the storage, the portable memory medium may be sent by mail or directly handed over through a person.

In the service center 30, the CONDITION information is collected by any collecting unit, such as, for example, the connection unit 37 or a memory medium driver. The collected CONDITION information is stored in the medical equipment condition database 32 by the system control unit 31. Prior to the storage, the system control unit 31 may process some of the collected CONDITION information. For example, the system control unit 31 accumulates the powered time or adds the newly collected powered time to the already accumulated powered time recorded in the operating condition managing table 322. Also the system control unit 31 specifies the maximum and minimum temperatures, recognizes the time when the maximum and minimum temperatures are recorded, calculates the average temperature, and the like. The result of the processing is stored in the medical equipment condition database 32 as CONDITION information.

Whether the service center 30 collects the CONDITION information or the like from the hospital 20 in every power-off of the medical equipment 11, in every one day, or once in a predetermined period, the CONDITION information in the medical equipment condition database 32 may, not be limited to, but preferably be stored in a unit of one day or any other constant interval.

Figure 10:
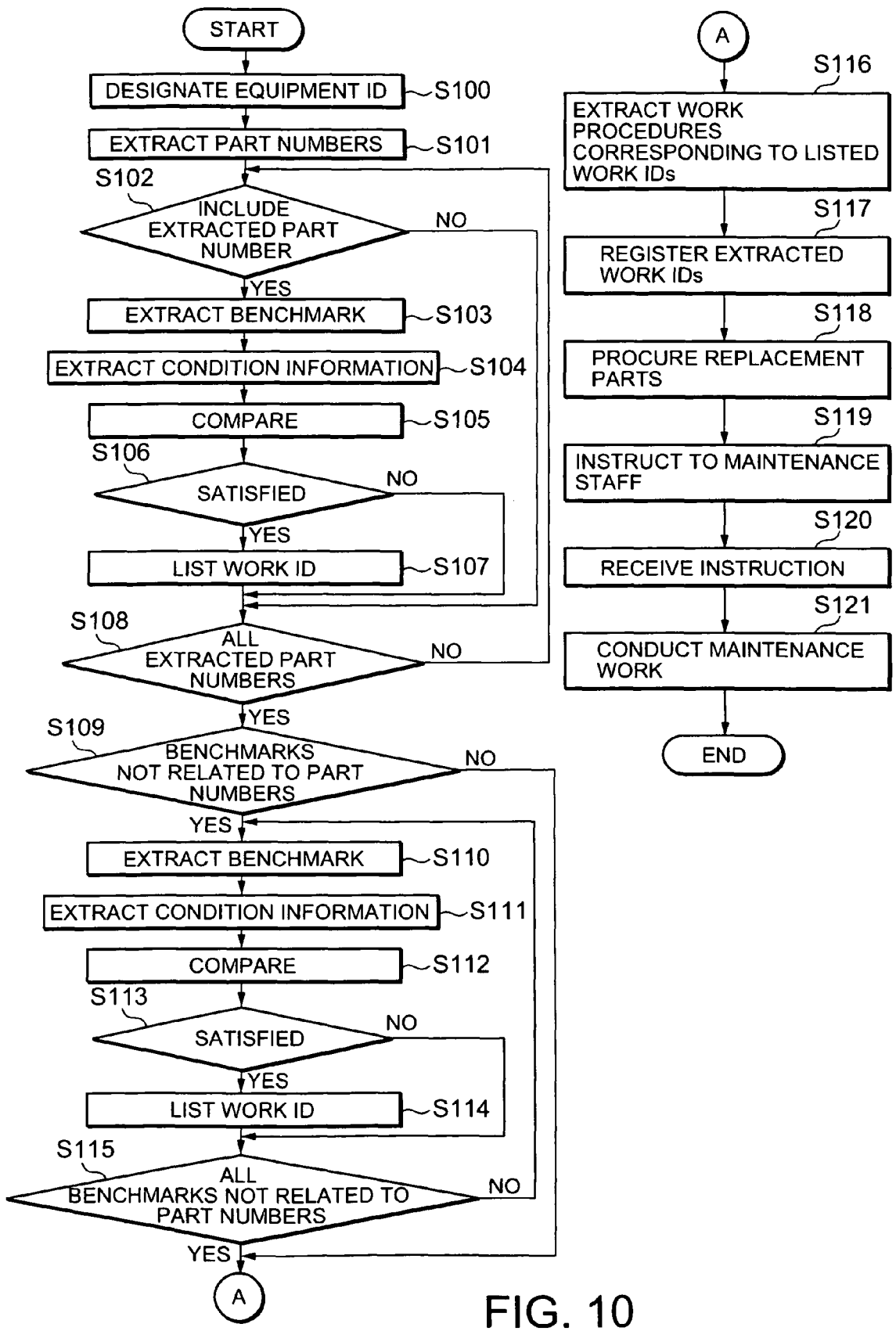
FIG. 10 is a flowchart for explaining an example of an operation flow in the maintenance system according to the embodiment.

FIG. 10 is a flowchart for explaining an example of an operation flow in the maintenance system according to the embodiment.

The system control unit 31 may extract one or more work IDs based on the information stored in the medical equipment condition database 32 and the work procedure database 33, that is, based on the installed condition of the medical equipment 11. The extraction may be conducted at predetermined periodic service intervals, for example, every three months or every four months. The extracted work IDs or information of the maintenance works identified by the extracted work IDs are provided as maintenance work instruction or part of the instruction of the medical equipment 11 from the work procedure instruction unit 35 (as a provider) to the maintenance work terminal 40 held by the maintenance staff through the connection unit 37 and the communication network 20. In providing to the maintenance work terminal 40, only a number uniquely identifiable of a group including one or more maintenance works may be provided, instead of the work IDs or the information. The uniquely identifiable number may be, for example, a periodic service ID. In this case, the maintenance staff operates the maintenance work terminal 40 so that the maintenance work terminal 40 accesses to the work management WEB server 36 (as a provider) and obtains information of the work IDs based on the provided uniquely identifiable number.

A flow from work ID designation to conducting the maintenance work will be explained with reference to FIG. 10 below.

At a predetermined or scheduled periodic service time, the operator may input a periodic service ID and an equipment ID identifying the medical equipment 11 from an input terminal (as a designator) provided in the service center 30. The equipment ID is input to the system control unit 31 as designation of the equipment ID identifying the medical equipment 11 to conduct the maintenance works (step S100). Alternatively, if the system control unit 31 includes a feature of determining the periodic service time, the system control unit 31 may determine the periodic service time of the medical equipment 11 and designate the equipment ID for the maintenance works (as a designator). Further alternatively, the system control unit 31 may receive the designation of the equipment ID from other unit or apparatus which manages the periodic service time through the connection unit 37 (as a designator).

When the equipment ID is designated, the system control unit 31 accesses to the medical equipment condition database 32 and further accesses to the replacement part managing table 321 in FIG. 2 stored in the medical equipment condition database 32. In the replacement part managing table 321, the system control unit 31 accesses to a table identified by the designated equipment ID (e.g., the designated equipment ID:002523) The system control unit 31 extracts part numbers which are being used in the medical equipment 11 at the time of access and stores the extracted part numbers (step S101).

In the part numbers 3212, each of all or some of part numbers include a revision mark. Therefore, since the revision mark is updated, for example, from A to B when the part is replaced at the time of a periodic service, different revision marks may be given even to the same number. Therefore, the system control unit 31 extracts part numbers given the revision mark which have been most recently updated if there are stored more than one same numbers in the part numbers 3212. When some parts have not been replaced, part numbers identifying such parts provided at the installation of the medical equipment 11 are extracted by the system control unit 31. In the part number extraction, the manufacture serial numbers may also be considered. For example, a condition extracting part numbers given a predetermined manufacture serial number or less may be considered for the extraction.

When the part numbers are extracted, the system control unit 31 accesses to the work procedure database 33. The system control unit 31 refers to the part number 3311 in the benchmark table 331 and determines whether the extracted part numbers are included in the part numbers 3311 (step S102). This determination is conducted with respect to each of the extracted part numbers.

If the extracted part number is included in the part numbers 3311, the system control unit 31 extracts the benchmark information 3312 recorded in correspondence with the part number 3311 identical to the extracted part number (step S103). The benchmark information 3312 includes the reference information and information of the medical equipment 11 (CONDITION information) to be compared to the reference information Therefore, the system control unit 31 accesses to the medical equipment condition database 32 and further accesses to the operating condition managing table 322, the environmental condition managing table 323, or the quality managing table 324, which stores the CONDITION information regarding the extracted benchmark information 3312. Accordingly, the system control unit 31 extracts the CONDITION information regarding the extracted benchmark information 3312 (step S104).

The system control unit 31 compares the extracted CONDITION information to the reference information in the benchmark information 3312 (step S105). As a result of the comparison, the system control unit 31 determines whether the condition of the benchmark information is satisfied or not (step S106). When it is satisfied, the system control unit 31 extracts the work ID 3313 recorded in correspondence with at least one of the part numbers 3311 or the benchmark information 3312. The extracted work ID is written in a maintenance work list (step S107). This maintenance work list is what is provided to the maintenance staff and may be prepared in the work management WEB server 36.

When the work ID has been written in the maintenance work list, the system control unit 31 determines whether steps S102 to S107 have been done for all the part numbers extracted in step S101 (step S108). Also when it is determined that the condition is not satisfied in step S106 or when it is determined that the extracted part numbers are not included in the part numbers 3311 in step S102, the system control unit 31 determines whether steps S102 to S107 have been done for all the part numbers extracted in step S101.

If it is not completed yet for all the part numbers extracted in step S101, the flow goes back to step S102 and steps S102 to S107 may be repeated. In the event of the completion, the system control unit 31 accesses to the work procedure database 33 and refers to the benchmark table 331 again. The system control unit 31 determines whether there is stored benchmark information 3312 which does not have corresponding part numbers 3311 in rows 3314 or not (step S109).

If the benchmark information 3312 is recorded in the rows 3314, the system control unit 31 extracts the benchmark information 3312 recorded in the rows 3314 (step S110). The system control unit 31 accesses to the medical equipment condition database 32 and further accesses to the environmental condition managing table 323, the quality managing table 324, or the like which records the CONDITION information regarding the extracted benchmark information 3312. Accordingly, the system control unit 31 extracts the CONDITION information regarding the extracted benchmark information 3312 (step S111).

The system control unit 31 compares the extracted CONDITION information to the reference information in the benchmark information 3312 (step S112). As a result of the comparison, the system control unit 31 determines whether the condition of the benchmark information is satisfied or not (step S113). When it is satisfied, the system control unit 31 extracts the work ID 3313 recorded in correspondence with the benchmark information 3312. The extracted work ID is written in the maintenance work list (step S114).

When the work ID has been written in the maintenance work list, the system control unit 31 determines whether steps S110 to S114 have been done for all the benchmark information in the rows 3314 (step S115). Also when it is determined that the condition is not satisfied in step S113, the system control unit 31 determines whether steps S110 to S114 have been done for all the benchmark information in the rows 3314. If it is not completed yet for all the benchmark information in the rows 3314, the flow goes back to step S110 and steps S110 to S114 may be repeated.

In the event of the completion, the system control unit 31 accesses to the work management WEB server 36 so as to obtain the work IDs written in the maintenance work list in step S107 and/or step S114. The system control unit 31 then accesses to the work procedure database 33 and refers to the work procedure table 332. The system control unit 31 extracts the work procedure references 3322, the part replacement 3323, the part numbers 3324, the standard work time 3325, the concurrent work IDs 3326, and the like which correspond to the work IDs 3321 identical to the listed work IDs as the information of the maintenance work (step S116).

Also when it is determined that the benchmark information 3312 is not stored in the rows 3314 in step S109, step S116 is conducted.

The information of the maintenance work extracted in step S116 is stored in the work procedure instruction unit 35 so as to be ready to be provided as the maintenance work instruction (step 117). In the event that the periodic service ID is sent to the maintenance work terminal 40, the information of the maintenance work may be stored in the work procedure instruction unit 35 as information to be obtained through the identification by the periodic service ID.

When the maintenance work instruction is stored in the work procedure instruction unit 35, the system control unit 31 accesses to the work procedure instruction unit 35 and extracts (the part replacement information and) the part numbers included in the maintenance work instruction. The system control unit 31 prepares a part arrangement list identifiable by the equipment ID with respect to the extracted part numbers. The part arrangement list is sent to a part procurement department in the service center 30 in order to request an arrangement and procurement of replacement parts and/or particular materials (step S118). If the system control unit 31 manages or can obtain stock information of the parts or the like, the system control unit 31 may be allowed to automatically order parts identified by the part numbers included in the part arrangement list which are not in stock.

Also when the maintenance work instruction is stored in the work procedure instruction unit 35, an instruction is transmitted to the maintenance work terminal 40 from the work procedure instruction unit 35 through the connection unit 37 and the communication network 20 by, for example, electronic mail (email) so that the maintenance staff can be instructed to conduct the periodic service (step S119). This transmitted instruction may include the periodic service ID or the maintenance work instruction. The transmitted instruction may also include information of when the replacement parts or the like are expected to be available Further on the basis of this expected date, the transmitted instruction may also include information of when the maintenance staff may actually be able to start the maintenance work.

The transmitted instruction is received by the maintenance work terminal 40 so that the maintenance staff can obtain the work procedure references, the part replacement information, the part numbers, the standard work time, the concurrent work IDs, the expected arrival date of the replacement parts, the possible starting date the maintenance work, and the like, with respect to the maintenance work of the medical equipment 11 identified by the equipment ID (step S120).

The maintenance staff may discuss the periodic service with a staff of the hospital 10 and determines the date and time for the periodic service based on the received instruction. In the discussion, the maintenance staff may present the starting time and the finishing time of the maintenance works of the periodic service based on estimated required time calculated, for example, by subtracting the standard work time for maintenance works identified by the concurrent work IDs from a sum of the standard work time for the maintenance works included in the maintenance work instruction. The maintenance staff will conduct the instructed maintenance works as the periodic service at the determined time of the determined date (step S121).

According to the above flow, the maintenance works may be conducted in accordance with the configuration of the medical equipment 11 at the time of the maintenance service. That is, the maintenance works may be conducted in accordance with an actual configuration of the medical equipment at the time of the maintenance service, which may be different from at the time of the installation since some parts and/or units may have been replaced in response to the failure occurrence or in the updating. Further, the maintenance works are determined in consideration of operating conditions or the like of the medical equipment 11. Therefore, it may be possible to conduct individual or a sort of custom-made maintenance works for the medical equipment 11.

In addition to the maintenance works described above, ordinary maintenance works instructed in the maintenance service instruction manual may also be conducted. In this case, it may happen that one maintenance work determined according to the embodiment and one ordinary maintenance work pertain to the same one or more work subjects. If concrete works in their maintenance works are different for the common subject(s), the maintenance work determined according to the embodiment may be provided to the maintenance staff in preference to the ordinary maintenance work. Alternatively, the maintenance work determined according to the embodiment may be instructed to be conducted by priority while the maintenance staff is provided with both the maintenance work determined according to the embodiment and the ordinary maintenance work.

The maintenance work terminal 40 can display the work procedure references, work procedure documents or service instruction manuals, the part replacement information, the part numbers, the standard work time, the concurrent work IDs, and the like through the communication network 20. Therefore, the maintenance staff can easily refer to such information at the place of the maintenance works, for example, where the medical equipment 11 is installed.

The maintenance staff may be allowed to inquire additional reference data of the medical equipment 11, information of different part of the work procedure document, and the like, in addition to the provided work procedure document and the like, to databases in the service center 30, by operating the maintenance work terminal 40 even at the place of the maintenance works. Accordingly, even if it is a maintenance staff who is not a full-time maintenance staff of the medical equipment 11 and not familiar with medical equipment 11, the maintenance staff may be able to obtain as much information of the medical equipment 11 as the full-time maintenance staff and to conduct the maintenance works.

The maintenance staff may sometimes need to or be asked by the staff of the hospital 10 to explain the necessity of the periodic service or why a particular maintenance work is needed. In these cases, the maintenance staff may be able to explain the necessity by presenting the CONDITION information as numerical data of the medical equipment 11.

Figure 11:
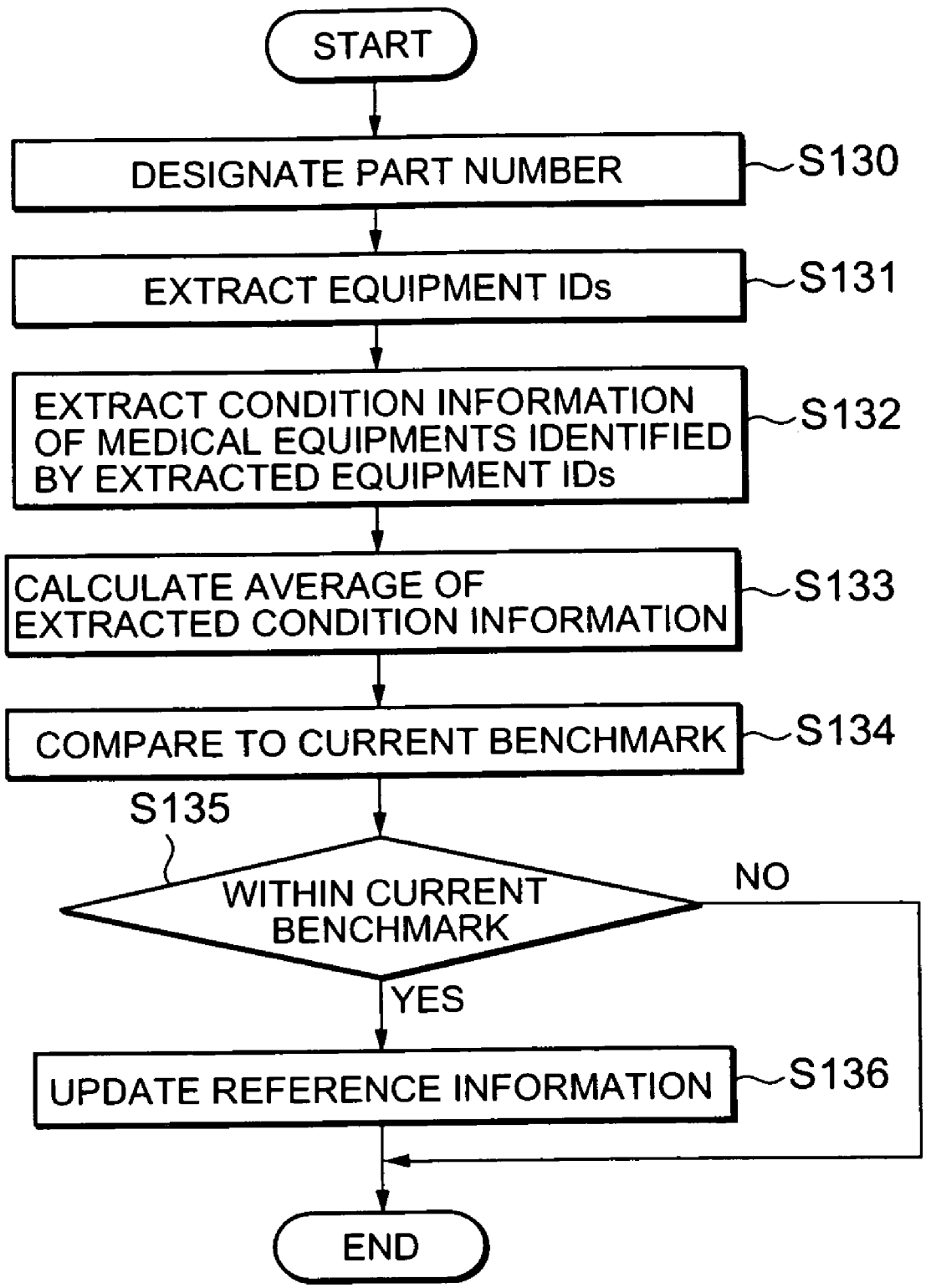
FIG. 11 is a flowchart showing an example of an updating flow of the benchmark table according to the embodiment.
Figure 12:
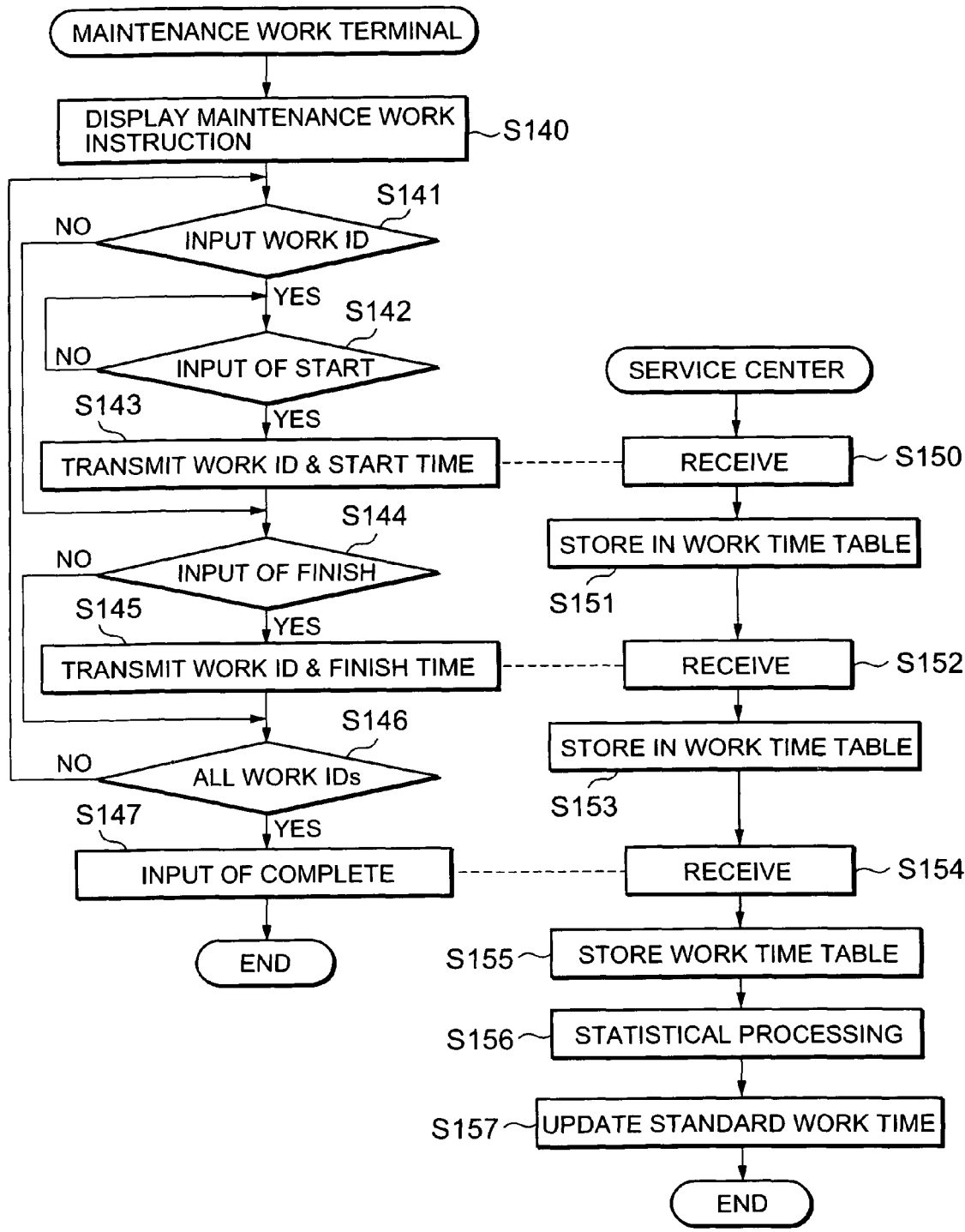
FIG. 12 is a flowchart showing an example of an updating flow of the procedure table according to the embodiment.

Next, updating tables stored in the medical equipment condition database 32 will be described with reference to FIGS. 11 and 12.

Updating the benchmark information 3312 of the benchmark table 331 will be first explained with reference to FIG. 11. FIG. 11 is a flowchart showing an example of an updating flow of the benchmark table 331 according to the embodiment.

The reference information of the benchmark information 3312 is compared to the CONDITION information of the medical equipment as described in the above embodiment. Whether the maintenance work should be conducted or not is determined as a result of the comparison. The reference information may typically be determined to be a safe value with a certain margin in order to avoid a risk of frequent occurrence of failures. This means that the benchmark information may not be so practical. Therefore, it may be preferable to prepare the benchmark information including the reference information which is more based on practical conditions of the medical equipment.

The following description is an example of updating the benchmark information 3312, more concretely, the reference information of the benchmark information 3312, based on the CONDITION information of the medical equipment 11 and other medical equipments in the same series or type of the medical equipment 11 (or other medical equipments similar to the medical equipment 11).

The following operation may be initiated when the operator in the service center 30 inputs to designate a specific part number or to update the benchmark information. The system control unit 31 determines the designation. The following operation may alternatively be initiated in response to the determination of the system control unit 31 that a predetermined date (and time) has come.

The system control unit 31 accesses to the work procedure database 33 and designates the part number 3311 identical to the input specific part number or selects any one of the part numbers 3311 (step S130). Instead of designating the part number 3311, the benchmark 3312 or the work ID 3312 may be designated and accordingly the corresponding part number 3311 may be designated.

In the event of the benchmark information 3312 in the row 3314, the system control unit 31 may designate any one of the benchmark information 3312. The system control unit 31 extracts information type or subject (e.g., image quality parameter B: Type 1) to be compared to the reference information included in the designated benchmark information 3312. Also in this case, the operator may input to designate specific one of the benchmark information 3312.

In response to the designation of the part number, the system control unit 31 accesses to the failure record database 34 and extracts, for example, all the equipment IDs recorded in correspondence with the failure part numbers 3412 identical to the designated part number from the failure record table 341 (step S131). At the same time, information of the failure date 3411 recorded in correspondence with the extracted equipment IDs 3414 is also extracted.

In the event that the information type or a subject to be compared to the reference information is extracted with respect to the benchmark information in the row 3314, the system control unit 31 extracts, for example, all the equipment IDs recorded in correspondence with the quality deteriorated subjects 3413 identical to the extracted information type or subject. At the same time, information of the failure date 3411 recorded in correspondence with the extracted equipment IDs 3414 is also extracted.

After the extraction of one or more equipment IDs, the system control unit 31 accesses to the medical equipment condition database 32 and extracts CONDITION information of medical equipments identified by the extracted equipment IDs from the operating condition managing table 322, the environmental condition managing table 323, the quality managing table, and the like (step S132). The CONDITION information to be extracted with respect to one medical equipment is one on the date identical to the extracted failure date of the one medical equipment. In the case there is no CONDITION information on the identical date, CONDITION information on the date just before the extracted failure date may be extracted.

The system control unit 31 obtains the CONDITION information of the medical equipments identified by the equipment IDs in step S132. The system control unit 31 calculates an average value (and a dispersion value) of the obtained CONDITION information for each CONDITION information type (step S133). That is, the average values are calculated for the accumulated powered time, the accumulated X-ray radiation time, the accumulated rotation numbers, the temperature, the humidity, the image quality parameters, and the like, respectively.

The system control unit 31 compares each of the calculated values to the benchmark information 3312 recorded in the benchmark table 331 at the time of the calculation (i.e., current benchmark information) (step S134). If the calculated CONDITION information satisfies the current benchmark information (step S135), the system control unit 31 replaces the current reference information with the calculated CONDITION information (calculated value). Since the result of the comparison in step S135 indicates that the current benchmark information has been set with too much margin for safety, the replaced benchmark information can be more practical. The comparison in step S135 and the replacement (if necessary) are conducted on every calculated CONDITION information. After the replacement, updating the reference information (or the benchmark information) is completed (step S136).

As an alternative example, the comparison result in step S135 may lead to the opposite action. That is, if the calculated CONDITION information satisfies the current benchmark information in step S135, the system control unit 31 does not replace the current reference information with the calculated CONDITION information (calculated value). When the benchmark information is not satisfied, the current reference information may be replaced with the calculated CONDITION information. This is based on the reason that the current benchmark information does not appropriately cover all the necessary range of replacement in practice. In other words, if actual CONDITION information falls in between the current reference information and the calculated CONDITION information, it results in that the maintenance work is not conducted on the part although the calculated CONDITION information shows that there is possibility that such a condition may be likely to cause a problem.

Also alternatively, steps S134 and S135 may be removed so as to always replace the current reference information with the calculated CONDITION information whatever the current benchmark information is.

The updating of the benchmark information may be conducted once in predetermined months in which the predetermined number of failure data may be collected with respect of one part number. For example, when the benchmark information is updated every three months or four months, it may be possible to match the period with a typically determined interval of periodic services.

When the extracted CONDITION information includes a piece of information showing a peculiar value with respect to one information type or subject (e.g., the temperature), such peculiar value may be removed from the average calculation. Also in this case, the system control unit 31 may treat exceptionally or inspect other extracted CONDITION information originated from a medical equipment which presented the peculiar value. The system control unit 31 may also control that information of such a medical equipment, its equipment ID, a part, and/or part number can be provided to the maintenance work terminal 40 so as to draw an attention of the maintenance staff.

According to the updating of the benchmark information, it may be avoidable of unnecessarily replacing parts or failing to conduct necessary part replacement. This results in conducting the maintenance works in the periodic service more practically and efficiently. The flowchart shown in FIG. 11 may be terminated for each part number or may sequentially be executed for all the subject part numbers.

Updating the standard work time 3325 of the work procedure table 332 will be explained with reference to FIG. 12. FIG. 12 is a flowchart showing an example of an updating flow of the procedure table 332 according to the embodiment.

The standard work time may be considered when the maintenance staff estimates and determines a whole time required for the periodic service. In other words, the periodic service includes a plurality of maintenance works and a whole estimated time of the periodic service may be an accumulated time of standard work time of the plurality of maintenance works. If each standard work time is so different from an actual required time, a whole time actually spent for the periodic service may happen to be very different from the estimated time. This means that the periodic service can not be completed as scheduled, which may trouble the hospital 10. The maintenance staff, the service center 30, the medical equipment manufacturer, and/or the like may lose trust of the hospital 10. Therefore, it is preferable that the standard work time is close to the time to be actually spent in the maintenance work.

The following description is an example of updating the standard work time 3325 based on the actual time which the maintenance staff spent in the maintenance works.

The maintenance staff gets to the medical equipment 11 for the periodic service at the time of the date determined in the discussion with the staff of the hospital 10. The maintenance staff operates the maintenance work terminal 40 before starting the maintenance works. In response to the operation, the maintenance work instruction, for example, identified by the periodic service ID received in advance is displayed in the maintenance work terminal 40 (step S140) Alternatively, the maintenance work instruction, for example, identified by the periodic service ID and updated with respect to information of the replacement parts may be transmitted from the work procedure instruction unit 35 to the maintenance work terminal 40 through the connection unit 37 and the communication network 20 in accordance with a request from the maintenance work terminal 40. Accordingly, the transmitted maintenance work instruction may be displayed in the maintenance work terminal 40.

The maintenance staff looks at the displayed maintenance work instruction and confirms the equipment IDs identifying maintenance works to conduct. The concurrent work IDs may also be considered at the same time. The maintenance staff then selects one of the work IDs to conduct first and inputs to determine the selected work ID, using an input device such as a mouse or a keyboard of the maintenance work terminal 40. In response that a control section of the maintenance work terminal 40 recognizes the determination input (step S141), the control section determines whether an input is made to start the maintenance work or not (step S142) When, for example, the maintenance staff operates to click on an icon of 'start' displayed in a display of the maintenance work terminal 40, the control section recognizes the input. In response to the recognition, information of start time of the maintenance work is transmitted with the determined work ID (step S143). When the maintenance work instruction is related to the periodic service ID, information of the periodic service ID may also be transmitted simultaneously.

The information of start time may indicate, for example, a concrete hour when the maintenance work terminal 40 includes a clocking feature. Also, for example, when the maintenance work terminal 40 does not include the clocking feature but a timer feature, the information of start time may indicate zero (0). In this case, the maintenance work terminal 40 starts to measure time in response to the recognition by the control section. If the maintenance work terminal 40 includes neither the clocking feature nor the timer feature, information indicating the start (e.g., flag information indicating one (1)) may be transmitted with the determined work ID. In this case, information of hour when the flag information was received or information of time zero (0) may be added to the received information in the service center 30. When the information of time zero (0) is added, time measurement is required in the service center 30.

The transmitted information of the start time and the work ID in step S143 is received by the connection unit 37 through the communication unit 20 (here, for example, the Internet) (step S150). The received information is input to the work management WEB server 36. In the work management WEB server 36, the information of the start time and the work ID is stored in a work time table prepared in the work management WEB server 36 (step S151).

If the maintenance staff inputs another work ID which can be conducted concurrently with the determined work ID based on the concurrent work IDs 3326, the operation for another work ID will follow steps S141 to S143, S150, and S151 as described above.

When the maintenance staff has finished the maintenance work identified by the determined work ID, for example, the maintenance staff operates to click on an icon of 'finish' displayed in the display of the maintenance work terminal 40. The control section of the maintenance work terminal 40 recognizes the input (step S144). In response to the recognition, information of finish time of the maintenance work is transmitted with the determined work ID (step S145).

The information of finish time may indicate, for example, a concrete hour when the maintenance work terminal 40 includes a clocking feature. Also, for example, when the maintenance work terminal 40 does not include the clocking feature but a timer feature, the information of finish time may indicate an elapsed time measured by the timer feature from the time of the recognition of the input 'start'. If the maintenance work terminal 40 includes neither the clocking feature nor the timer feature, information indicating the finish (e.g., flag information indicating zero (0)) may be transmitted with the determined work ID. In this case, information of hour when the flag information was received or information of an elapsed time from the reception of the information indicating time zero (0) in step S150 may be added to the received information in the service center 30.

The transmitted information of the finish time and the work ID in step S145 is received by the connection unit 37 through the communication unit 20 (here, for example, the Internet) (step S152). The received information is input to the work management WEB server 36. In the work management WEB server 36, the information of the finish time is stored in the work time table in correspondence with the information of the start time and/or the determined work ID (step S153).

According to the above flow, the maintenance work for one of the work IDs (i.e., the determined work ID) is completed. If the maintenance works (or steps S141 to S145 and S150 to S153) have not been completed for all the work IDs in the maintenance work instruction (step S146), steps S141 to S145 and S150 to S153 may be repeated for the next work ID.

When steps S141 to S145 and S150 to S153 have been completed for all the work IDs in the maintenance work instruction, the maintenance staff inputs to indicate the completion, for example, using the input device such as a mouse or a keyboard of the maintenance work terminal 40. The input information is recognized by the control section of the maintenance work terminal 40 and is transmitted (step S147).

The transmitted information of the completion in step S147 is received by the connection unit 37 through the communication unit 20 (here, for example, the Internet) (step S154). The received information is input to the work management WEB server 36. In the work management WEB server 36, the work time table storing the work ID, the start time, and the finish time is stored (step S155).

Steps S140 to S147 and S150 to S155 may be repeated in periodic services for only the medical equipment 11 or both the medical equipment 11 and other medical equipments in the same series or type of the medical equipment 11 (other medical equipments similar to the medical equipment 11). Accordingly, similar information is accumulated with respect to a plurality of maintenance works identified by each work ID.

In the service center 30, the system control unit 31 accesses to the work management WEB server 36 and obtains the information of the start time and the finish time with respect to a work ID. Based on the obtained information, the system control unit 31 calculates work time of each of the plurality of the maintenance works with respect to the work ID. Further, the system control unit 31 statistically processes the work time calculated for the plurality of the maintenance works (step S156). The result of the statistical processing can be used as an updated standard work time. The statistical processing is, for example, an average processing.

The statistical processing may be executed at predetermined intervals or every time when the information of the start time and the finish time for the predetermined times of the maintenance works is accumulated with respect to one work ID. After such information is accumulated for the predetermined times of the maintenance works, information of the oldest maintenance work stored in the work time table may be removed from the statistical processing while information of the latest maintenance work is used, instead. Or information of the oldest maintenance work stored in the work time table and to be used for the statistical processing may be removed from the statistical processing while information of the latest maintenance work is used, instead.

When the updated standard work time is obtained in the above manner, the system control unit 31 accesses to the work procedure database 33 and further to the work procedure table 332. The system control unit 31 completes the updating processing by replacing the current standard work time recorded in correspondence with the work ID with the updated standard work time (step S157).

By updating the standard work time, it may be possible to estimate standard work time for the maintenance work or a whole time of the periodic service which the maintenance staff will actually conduct. Therefore, the maintenance staff may be able to explain adequately to the staff of the hospital 10 how much the periodic service will influence clinical service or examination service in the hospital 10. This may result in improving relationship of trust with the hospital 10.

According to the embodiment described above, the maintenance works to be provided to the maintenance staff can be determined based on the benchmark information in line with configuration condition, operating condition, performance condition, installation condition, environmental condition, and the like of the medical equipment 11. The instructed maintenance works can be provided to and be conducted by the maintenance staff. Therefore, it can reduce failures and deterioration of features and quality before they happen.

Also the maintenance staff can be provided with concrete work information and can accordingly conduct the maintenance staff appropriately, irrespective of skills of the maintenance staff. Therefore, it may be possible to stably maintain the quality of the maintenance service.

In the above embodiment, the CONDITION information to be stored in the medical equipment condition database 32 has been described by taking an example of the information of the X-ray CT apparatus as shown in the operating condition managing table 322, the environmental condition managing table 323, and the quality managing table 324. The CONDITION information may alternatively or additionally include the following information.

When the medical equipment 11 is an X-ray CT apparatus, operating condition information to be stored, for example, in the operating condition managing table 322 may include information of at least one of the powered time, the X-ray radiation time, the number of rotation, X-ray tube voltage, and X-ray tube current. The environmental condition information to be stored, for example, in the environmental condition managing table 323 may include information of at least one of temperature and humidity of an operation room, temperature of a scan room, and temperature in an inlet of the gantry. Performance information to be stored, for example, in the quality managing table 324 may include information of at least one of slice thickness and positioning, CT number accuracy, low-contrast resolution, high-contrast (spatial) resolution, and image uniformity.

When the medical equipment 11 is an MRI apparatus, the operating condition information may include information of powered time. The environmental condition information may include information of at least one of temperature and humidity of an operation room, temperature of a scan room, and temperature in an inlet of the gantry. The performance information may include information of at least one of technologist's weekly QC test, center frequency, table positioning, setup and scanning, geometric accuracy, high-contrast resolution, and low-contrast resolution.

When the medical equipment 11 is an X-ray diagnosis apparatus (e.g., an X-ray angiography apparatus), the operating condition information may include information of at least one of powered time, X-ray radiation time, X-ray tube voltage, and X-ray tube current. The environmental condition information may include information of at least one of temperature and humidity of an operation room, temperature of a scan room, and temperature in an inlet of the gantry. The performance information may include information of at least one of minimum detectable contrast (%), low-contrast resolution (contrast-detail), optical density, high-contrast resolution, and entrance skin dose.

When the medical equipment 11 is an ultrasound diagnosis apparatus, the operating condition information may include information of at least one of powered time and using time of an ultrasonic probe (i.e., ultrasound generating time). The environmental condition information may include information of at least one of temperature and humidity of an operation room, temperature of a scan room, and temperature in an inlet of the gantry. The performance information may include information of at least one image quality parameter of system sensitivity and/or penetration capability, image uniformity, and low-contrast object detectability (optional).

The embodiments described above are examples described only for making it easier to understand the present invention, and are not described for the limitation of the present invention. Consequently, each component and element disclosed in the embodiments of the present invention may be redesigned or modified to its equivalent within a scope of the present invention Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. A method of managing at least one maintenance work on medical diagnosis equipment installed in a medical facility, the method comprising:
   collecting condition information of the medical diagnosis equipment, the condition information including operating condition information of the medical diagnosis equipment;
   determining, by a system control unit of a service center, that maintenance work on the medical equipment should be performed when the collected condition information exceeds reference information;

providing maintenance staff with information of the determined maintenance work; and updating the reference information by calculating an average value of the condition information at a time of failure of the medical diagnosis equipment and condition information of other medical diagnosis equipment similar to the medical diagnosis equipment, comparing the calculated average value to the reference information, and replacing the reference information with the calculated average value when the calculated average value is less than the reference information.

2. The method according to claim 1, wherein the information of the determined maintenance work includes at least one of information of a part on which the determined maintenance work is to be conducted and information of a work procedure.

3. The method according to claim 1, wherein, when a plurality of the maintenance work is determined, the information of the determined maintenance work includes information identifying another determined maintenance work which can be concurrently conducted with the determined maintenance work.

4. The method according to claim 1, wherein the information of the determined maintenance work includes information of a standard work time required for the maintenance work.

5. The method according to claim 4, wherein the information of the standard work time is updated based on past actual work time spent on conducting the maintenance work.

6. The method according to claim 1, wherein the condition information further includes at least one of environmental condition information and performance information of the medical equipment.

7. The method according to claim 6, wherein the medical diagnosis equipment is an X-ray CT apparatus, and the operating condition information includes information of at least one of an accumulated powered time, X-ray radiation time, X-ray tube voltage, X-ray tube current, and a number of gantry rotation of the X-ray CT apparatus.

8. The method according to claim 6, wherein the medical equipment is an MRI apparatus, and the operating condition information includes information of an accumulated powered time of the MRI apparatus.

9. The method according to claim 6, wherein the medical diagnosis equipment is an X-ray diagnosis apparatus, and the operating condition information includes information of at least one of an accumulated powered time, X-ray radiation time, X-ray tube voltage, and X-ray tube current of the X-ray diagnosis apparatus.

10. The method according to claim 6, wherein, the medical diagnosis equipment is an ultrasound diagnosis apparatus, and the operating condition information includes information of an ultrasound generating time of the ultrasound diagnosis apparatus.

11. The method according to claim 6, wherein the environmental condition information includes information of at least one of temperature and humidity.

12. The method according to claim 6, wherein the performance information includes information of an image quality parameter of the medical diagnosis equipment.

13. The method according to claim 1, wherein the providing step includes storing the information of the determined maintenance work in a WEB server in an accessible manner for the maintenance staff.

14. The method according to claim 1, wherein the providing step includes transmitting the information of the determined maintenance work to a terminal of the maintenance staff through a communication line.

15. The method according to claim 1, wherein the providing step includes storing the information of the determined maintenance work in a portable memory medium.

16. A method of managing a maintenance work on medical diagnosis equipment installed in a medical facility, the method comprising:

designating equipment identification information identifying the medical equipment;

collecting condition information of the medical diagnosis equipment identified by the designated equipment identification information;

comparing the collected condition information to reference information;

determining, by a system control unit of a service center, work identification information identifying the maintenance work based on the comparison;

providing maintenance staff with information of the maintenance work identified by the determined work identification information; and updating the reference information by calculating an average value of the condition information at a time of failure of the medical diagnosis equipment and condition information of other medical diagnosis equipment similar to the medical diagnosis equipment, comparing the calculated average value to the reference information, and replacing the reference information with the calculated average value when the calculated average value is less than the reference information.

17. The method according to claim 16, wherein the step of collecting condition information includes collecting condition information of a part included in the medical equipment identified by the designated equipment identification information.

18. The method according to claim 17, wherein the information of the maintenance work includes part identification information identifying a part relating to the collected condition information compared to the reference information when the work identification information is determined based on the comparison.

19. The method according to claim 17, further comprising generating a list of part identification information identifying a part relating to the collected condition information compared to the reference information when the work identification information is determined based on the comparison.

20. The method according to claim 19, wherein the generated list of part identification information is compared to information of an in-stock part, and the part identified by the listed part identification information which is not included in the information of the in-stock part is automatically ordered.

21. The method according to claim 16, wherein the information of the maintenance work is provided for the maintenance work to be conducted periodically.

22. The method according to claim 16, wherein the information of the maintenance work identified by the determined work identification information is provided in preference to information of an ordinary maintenance work when the maintenance work identified by the determined work identification information and the ordinary maintenance work pertain to a same subject.

23. A maintenance system for managing at least one maintenance work on medical diagnosis equipment installed in a medical facility, the system comprising:

a collecting unit configured to collect condition information of the medical equipment, the condition information including operating condition information of the medical diagnosis equipment;

a memory configured to store the collected condition information;

a controller coupled to the collecting unit and configured to determine that maintenance work on the medical equipment should be performed when the collected condition information exceeds reference information, wherein the controller is configured to update the reference information by calculating an average value of the condition information at a time of failure of the medical diagnosis equipment and condition information of other medical diagnosis equipment similar to the medical diagnosis equipment, comparing the calculated average value to the reference information, and replacing the reference information with the calculated average value when the calculated average value is less than the reference information; and a provider coupled to the controller and configured to provide maintenance staff with information of the determined maintenance work.

24. The system according to claim 23, wherein the information of the determined maintenance work includes at least one of information of a part on which the determined maintenance work is conducted and information of a work procedure.

25. The system according to claim 23, wherein, when a plurality of the maintenance work is determined, the information of the determined maintenance work includes information identifying another determined maintenance work which can be concurrently conducted with the determined maintenance work.

26. The system according to claim 23, wherein the information of the determined maintenance work includes information of a standard work time required for the maintenance work.

27. The system according to claim 26, wherein the information of the standard work time is updated based on past actual work time spent on conducting the maintenance work.

28. The system according to claim 23, wherein the condition information further includes at least one of environmental condition information and performance information of the medical diagnosis equipment.

29. The system according to claim 28, wherein the medical diagnosis equipment is an X-ray CT apparatus, and the operating condition information includes information of at least one of an accumulated powered time, X-ray radiation time, X-ray tube voltage, X-ray tube current, and a number of gantry rotation of the X-ray CT apparatus.

30. The system according to claim 28, wherein the medical diagnosis equipment is an MRI apparatus, and the operating condition information includes information of an accumulated powered time of the MRI apparatus.

31. The system according to claim 28, wherein the medical diagnosis equipment is an X-ray diagnosis apparatus, and the operating condition information includes information of at least one of an accumulated powered time, X-ray radiation time, X-ray tube voltage, and X-ray tube current of the X-ray diagnosis apparatus.

32. The system according to claim 28, wherein, the medical diagnosis equipment is an ultrasound diagnosis apparatus, and the operating condition information includes information of an ultrasound generating time of the ultrasound diagnosis apparatus.

33. The system according to claim 28, wherein the environmental condition information includes information of at least one of temperature and humidity.

34. The system according to claim 28, wherein the performance information includes information of an image quality parameter of the medical diagnosis equipment.

35. The system according to claim 23, wherein the provider stores the information of the determined maintenance work in a WEB server in an accessible manner for the maintenance staff.

36. The system according to claim 23, wherein the provider transmits the information of the determined maintenance work to an terminal of the maintenance staff through a communication line.

37. The system according to claim 23, wherein the provider stores the information of the determined maintenance work in a portable memory medium.

38. A maintenance system for managing maintenance work on medical diagnosis equipment installed in a medical facility, the system comprising:

a designator configured to designate equipment identification information identifying the medical equipment;

a memory coupled to the designator and configured to store the equipment identification information, condition information of the medical equipment identified by the equipment identification information, benchmark information for comparing the condition information to reference information, and work identification information identifying the maintenance work resulting from a comparison based on the benchmark information in a related manner;

a controller coupled to the memory and configured to determine the work identification information based on the designated equipment identification information, wherein the controller is configured to update the reference information by calculating an average value of the condition information at a time of failure of the medical diagnosis equipment and condition information of other medical diagnosis equipment similar to the medical diagnosis equipment, comparing the calculated average value to the reference information, and replacing the reference information with the calculated average value when the calculated average value is less than the reference information; and a provider coupled to the controller and configured to provide maintenance staff with information of the maintenance work identified by the determined work identification information.

39. The system according to claim 38, wherein the memory further stores part identification information identifying a part included in the medical diagnosis equipment identified by the equipment identification information, and the benchmark information relates to the part identification information.

40. The system according to claim 38, wherein the memory further stores part identification information in relationship to at least one of the benchmark information and the work identification information, the part identification information identifying a part included in the medical diagnosis equipment identified by the equipment identification information, the part being associated with a result of the comparison based on the benchmark information, and the information of the maintenance work includes the part identification information related to at least one of the work identification information and the benchmark information resulting in the work identification information.

41. The system according to claim 38, wherein the memory further stores part identification information in relationship to at least one of the benchmark information and the work identification information, the part identification information identifying a part included in the medical diagnosis equipment identified by the equipment identification information, the part being associated with a result of the comparison based on the benchmark information, and a list of part identification information related to at least one of the work identification information and the benchmark information resulting in the work identification information.

42. The system according to claim 41, wherein the list of part identification information is compared to information of in-stock part and the part identified by the listed part identification information which is not included in the information of in-stock part is automatically ordered.

43. The system according to claim 38, wherein the information of the maintenance work is provided for the maintenance work to be conducted periodically.

44. The system according to claim 38, wherein the information of the maintenance work identified by the determined work identification information is provided in preference to information of an ordinary maintenance work when the maintenance work identified by the determined work identification information and the ordinary maintenance work pertain to a same subject.

* * * * *